US008771740B2

(12) United States Patent
Kerkhof

(10) Patent No.: US 8,771,740 B2
(45) Date of Patent: *Jul. 8, 2014

(54) PROCESS FOR PRODUCING NANOPARTICLES BY SPRAY DRYING

(76) Inventor: Nicholas J. Kerkhof, Burleson, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/438,240

(22) Filed: May 21, 2006

(65) Prior Publication Data

US 2006/0210640 A1 Sep. 21, 2006

Related U.S. Application Data

(63) Continuation-in-part of application No. 10/168,520, filed as application No. PCT/US00/34606 on Dec. 19, 2000, now Pat. No. 7,078,057.

(60) Provisional application No. 60/172,573, filed on Dec. 20, 1999.

(51) Int. Cl.

*A61K 9/14* (2006.01)
*B41L 1/28* (2006.01)
*A01N 43/04* (2006.01)
*A01N 43/30* (2006.01)
*A61K 31/56* (2006.01)

(52) U.S. Cl.

USPC ................. 424/489; 462/5; 514/23; 514/464; 514/178

(58) Field of Classification Search
None
See application file for complete search history.

(56) References Cited

U.S. PATENT DOCUMENTS

| | | | | |
|---|---|---|---|---|
| 3,771,237 A | 11/1973 | Hansen et al. | 34/57 A |
| 4,511,592 A | 4/1985 | Percel et al. | 426/646 |
| 4,689,297 A | 8/1987 | Good et al. | 435/171 |
| 4,849,227 A * | 7/1989 | Cho | 424/498 |
| 4,851,421 A | 7/1989 | Iwasaki et al. | 514/352 |
| 4,885,848 A | 12/1989 | Christensen | 34/57 R |
| 5,006,204 A | 4/1991 | Jensen | 159/3 |
| 5,015,480 A | 5/1991 | Childers et al. | 424/486 |
| 5,133,137 A | 7/1992 | Petersen | 34/57 A |
| 5,145,684 A | 9/1992 | Liversidge et al. | 424/489 |
| 5,325,606 A | 7/1994 | Liborius | 34/589 |
| 5,356,467 A * | 10/1994 | Oshlack et al. | 106/161.1 |
| 5,357,688 A | 10/1994 | Christensen | 34/369 |
| 5,392,531 A | 2/1995 | Christensen et al. | 34/583 |
| 5,411,750 A * | 5/1995 | Lajoie et al. | 424/717 |
| 5,510,118 A | 4/1996 | Bosch et al. | 424/489 |
| 5,573,783 A | 11/1996 | Desieno et al. | 424/490 |
| 5,591,733 A | 1/1997 | Bolger et al. | 514/172 |
| 5,955,448 A | 9/1999 | Colaco et al. | 514/53 |
| 6,862,890 B2 | 3/2005 | Williams et al. | 62/64 |
| 2003/0211162 A1 | 11/2003 | Kerkhof | 424/489 |

FOREIGN PATENT DOCUMENTS

| | | |
|---|---|---|
| EP | 0411629 A2 | 2/1991 |
| EP | 411629 A3 | 2/1991 |
| EP | 0411629 B1 | 11/1993 |
| EP | 611567 A1 | 8/1994 |
| JP | 11-005746 A | 1/1999 |
| WO | WO 9513867 | 5/1995 |
| WO | WO 9521617 | 8/1995 |
| WO | WO 9609814 | 4/1996 |
| WO | WO 9616076 | 5/1996 |
| WO | WO 9640628 | 12/1996 |
| WO | WO 97/13503 | 4/1997 |

OTHER PUBLICATIONS

Liversidge et al. "Particle size reduction for improvement of oral bioavailability of hydrophobic drugs: Absolute oral bioavailability of nanocrystalline danazol in beagle dogs" International Journal of Pharmaceutics 125 (1995) 91-97.*
International Search Report for PCT/US00/34606 completed on May 23, 2001.
Pharmaceutical Sciences 1990, Mack Publishing Company, pp. 1644-1647.
Krukonis, Supercritical Fluid Nucleation of Difficult-To-Comminute Solids, 1984.
International Search Report for International Application No. PCT/US07/12069.
Pharm. Ind., 1992, vol. 54, No 4, pp. 373-377, Youssef et al.

* cited by examiner

*Primary Examiner* — Michael G Hartley
*Assistant Examiner* — Nabila Ebrahim
(74) *Attorney, Agent, or Firm* — Winstead PC

(57) ABSTRACT

Nanoparticles of a compound are produced by spraying a solution of the compound into a heated chamber. The resulting product comprises a free flowing mixture of nanoparticles of the compound.

19 Claims, No Drawings

PROCESS FOR PRODUCING NANOPARTICLES BY SPRAY DRYING

CROSS REFERENCE TO RELATED APPLICATIONS

This application is a continuation-in-part of U.S. application Ser. No. 10/168,520 filed Oct. 18, 2002 now U.S. Pat. No. 7,078,057, which is the National Stage of International Application No. PCT/US00/34606, filed Dec. 19, 2000, which claims the benefit under 35 U.S.C. §119(e) of U.S. Provisional Application No. 60/172,573, filed Dec. 20, 1999.

BACKGROUND OF THE INVENTION

1. Field of the Invention

The present invention relates to methods for producing nanoparticles of compounds that are useful in pharmaceutical, food and cosmetic applications. Specifically, this invention is concerned with producing nanometer particles by utilizing a technique in which a solution comprising a solvent and a solute is spray dried in an empty chamber to form nanoparticles.

2. Related Art

Particles of compounds having low water-solubility are commonly used in a wide variety of applications, including ceramics, paints, inks, dyes, lubricants, pharmaceuticals, food products, pesticides, insecticides, fungicides, fertilizers, chromatography columns, cosmetics, lotions, ointments, and detergents. Aqueous dispersions of particles are used in many cases to avoid hazards such as flammability and toxicity associated with organic solvents. Such dispersions typically have a broad range of particle size.

In many cases product performance can be improved by controlling the particle size distribution. In general, smaller particles of a compound will dissolve faster than larger particles of the same compound. Control of particle size is, therefore, important in controlling the rate of solubilization.

Obtaining particle sizes in the nanometer range is often useful for enhancing the effectiveness of compounds. This is particularly true for compounds that are practically insoluble or slightly soluble in water. Nanometer particles provide a large specific surface area, leading to increased dissolution rate and bioavailability of pharmaceutical drug substance, digestibility of food ingredients, as well as functional effectiveness of cosmetic ingredients. In particular, reducing the particle size of practically insoluble or poorly-soluble drug substances has been shown to increase the dissolution rate and consequently, their bioavailability.

A limited number of methods are known in the art for producing materials having nanometer particle sizes. U.S. Pat. No. 5,145,684 to Liversidge et al., describes a method for forming nanoparticles of a water-insoluble drug by wet milling in the presence of a surfactant. Wet bead milling, in which the material, suspended in aqueous medium, is milled by using glass, polymer, aluminum, zirconium or other metal beads. The milling process can be performed in a roller mill, vibratory mill or high energy mechanical mill. A dispersion consisting of a liquid dispersion medium and the above-described particles is described as being stable. U.S. Pat. No. 5,510,118 to Bosch et al., describes a method for forming nanoparticles of a drug by high pressure homogenization. In this method, a suspension of the material is forced to pass through a narrow orifice by applying a high pressure. The high shear applied to the suspension reduces the particle size of the suspension.

With respect to wet bead milling, the batch size for roller or vibratory mills is limited by the size of the container on the mill. High energy mechanical milling is a continuous process capable of achieving nanometer particles in a short period of time. However, the beads are subjected to severe collisions with the metal chamber, such that abrasion could result in glass or metal contamination of the milled material.

The high pressure homogenization method described by Bosch et al. is usually used to reduce the size of liquid globules in dispersed systems, i.e., emulsions or liposomes. The success of high pressure homogenization method for solid materials is dependent on the physical property of the materials.

U.S. Pat. No. 4,851,421 to Iwasaki et al., discloses fine powders containing particles with a diameter of 0.5 micron or less that are formed by wet milling a dispersion liquid of a biocidal substance with a rigid media having a particle diameter of 0.5 mm or less. Biocidal substances include germicides, herbicides, insecticides, miticides and tickicides that are water-insoluble. Iwasaki et al. also disclose that the resulting biocidal fine powder can more promptly permeate through the surfaces of plants as well into insect bodies and microbe cells.

European application EP 0411629, describes a process whereby ultrafine particles of a slightly-soluble drug, whose average diameter is less than 2 to 3 µm, are obtained by milling the drug in the presence of a grinding aid selected from a sugar and a sugar alcohol. The weight ratio of said sugar or sugar alcohol is 2.5 to 50 parts by weight to one part of the drug, and the micronized drug has an average diameter of less than 1 µm.

In a spray-drying process, a dispersion of solid particles is finely sprayed into flowing warm air to afford dried powder of the material. The prior art versions of this technology do not reduce the particle size.

Spray drying consists of bringing together a highly dispersed liquid and a sufficient volume of hot air to produce evaporation and drying of the liquid droplets. In a typical spray drying process, the feed liquid may be a solution, slurry, emulsion, gel or paste, provided it is pumpable and capable of being atomized. A feed solution is sprayed into a current of warm, filtered air. The air supplies the heat for evaporation and conveys the dried product to a collector. The air is exhausted together with the moisture.

Spray-dried powder particles are homogeneous, approximately spherical in shape, nearly uniform in size. Lactose, mannitol, and flour are spray-dried for use in direct-compression tableting formulations.

Spray drying has also been previously employed to microencapsulate active agents for drug delivery. This use of spray drying comprises spraying a mixed solution of active agent and a co-ingredient that is able to form a matrix or shell around the active agent. PCT application WO96/09814, describes such a method to form spray-dried microparticles. One described embodiment is directed to microparticles comprising a low molecular weight drug and lactose. In one example, alcohol dehydrogenase (ADH) and lactose were spray dried to form microparticles (ADH 0.1% w/w; lactose 99.9% w/w). The microparticles were 4-5 µm in diameter, smooth and spherical, and contained air.

Despite the existence of known technologies, a need continues to exist in the field for a method of producing nanometer particles of compounds, where the method can conveniently be scaled up to production scale.

SUMMARY OF THE INVENTION

Embodiments of the invention disclosed herein are based upon the discovery that spray-drying technology can be employed to form nanometer particles. Nanometer particles of a compound are produced by spraying a solution of the compound into an empty heated chamber. The resulting product comprises nanometer-sized particles having a mean diameter no greater than 3 µm.

An embodiment of the invention relates to a method for producing nanoparticles of compounds that are useful in cosmetic, food and pharmaceutical applications. This embodiment of the invention is particularly useful for drug substances, since the administration of a drug compound in the form of nanoparticles greatly increases the bioavailability of the drug compound to the user.

An embodiment of the invention allows for the large scale production of nanoparticles.

An embodiment of the invention further provides a process for generating nanoparticles of a compound by spraying a solution of the compound into an empty heated chamber, without the need for a carrier or excipient molecule to be present within the chamber during the spray drying process.

In an embodiment of the invention, nanoparticles of a compound are obtained by spraying a solution of the compound into a heated, fluidized bed of carrier contained within a chamber.

In certain embodiments of the invention, an inert carrier or excipient molecule is included in the solution containing the compound to be spray dried. Doing so does not affect particle size of the compound, but enhances the dispersion and wettability of the resulting particulate material. Examples of suitable carrier molecules include, xylitol, mannitol, sorbitol, arabinose, ribose, xylose, glucose, mannose, galactose, sucrose, lactose, sodium lauryl sulfate, docusate sodium and hydroxy propyl methyl cellulose.

Other embodiments of the invention provide for the formation of nanoparticles that are suitable for administration to a user via oral gastrointestinal delivery, buccal delivery, sublingual delivery, pulmonary delivery, nasal delivery, vaginal delivery, rectal delivery, ocular delivery, otic delivery, epidermal delivery, dermal delivery or parenteral delivery.

The nanoparticles formed using process embodiments of the invention may be administered to a user in the form of tablets, capsules, powders, suspensions, emulsions, thin polymeric films and suppositories.

An embodiment of the invention allows for the formation of stable nanoparticles in the presence of surface active agents during processing.

DESCRIPTION OF EXEMPLARY EMBODIMENTS

The present invention is directed to a process for producing nanoparticles of a compound. The process comprises spraying a solution of a compound in a solvent, into an empty chamber under conditions that allow for a substantial amount of the solvent to be removed from said solution, such that nanometer-sized particles having a mean diameter no greater than 3 µm are formed.

The process according to the present invention, is generally carried out by spraying into a heated chamber a solution of a compound such that nanoparticles of a compound are formed. In an embodiment of the invention, the solution of compound is sprayed into an empty heated chamber. In this process, a compound that is to be nanosized, is mixed with an appropriate solvent to form a solution of the compound. The solution of the compound is subsequently sprayed into a heated chamber under conditions that allow for a substantial amount of the solvent to be removed from the solution. The nanoparticles generated by this process contain only the compound of interest.

A further embodiment of the invention provides a process for generating nanoparticles of a compound, wherein a solution of the compound is sprayed onto a fluidized bed of carrier particles. The bed is maintained at a temperature from about 20° C. to about 80° C., preferably about 25° C. to about 50° C. In other embodiments of the invention, the heated fluidized bed is maintained at a temperature between 27° C. to 48° C. The particle size of the carrier in the fluidized bed can range from about 10 µm to about 3 mm. In this process, the solution of compound is sprayed onto a fluidized bed of carrier particles, such that stable nanoparticles of compound are formed in a mixture with carrier particles.

In another embodiment of the invention, an inert carrier or excipient molecule is mixed with the solution containing the compound to be spray dried. This mixture is sprayed into a heated chamber. The nanoparticles formed in this process contain a mixture of compound and carrier. The amount of compound in a nanoparticle formed by this process can vary from less than 1% by weight to greater than 99% by weight. The remainder of the nanoparticle is comprised of carrier.

In an embodiment of the invention, one part of a compound is combined with about one (1) to about 100 parts by weight of a carrier. In another embodiment of the invention, 2.5 parts of a compound are combined with about 20 parts by weight of a carrier. In a further embodiment of the invention, 5 parts of a compound are combined with about 10 parts by weight of a carrier.

The nanoparticles formed by the disclosed processes have an average particle size (also known as mean diameter) ranging from about 50 nm to about 3000 nm. In certain embodiments of the invention the particle size of the compound ranges from about 50 nm to about 1000 nm. In other embodiments of the invention, the particle size of the compound ranges from about 200 nm to about 900 nm, and most preferably about 300 nm to about 800 nm.

The resulting nanoparticles are stable and do not appreciably flocculate or agglomerate. The compound may be water-soluble, or one that is poorly water soluble or substantially water insoluble. The nanoparticles can be formulated into pharmaceutical, cosmetic and food compositions that exhibit high bioavailability.

By stable, it is meant that the dispersion of nanoparticles exhibits no flocculation or particle agglomeration visible to the naked eye at least fifteen minutes, and preferably, at least two days or longer after preparation.

The process of the present invention is preferably employed with materials intended for diagnostic agents, pharmaceutical, food and cosmetic applications. Examples of nutritional agents appropriate for formulation as particulate suspensions include: betacarotene, vitamin A, vitamin B2, vitamin D, vitamin E, and vitamin K.

The processes described herein can be used with water soluble compounds, i.e., where the compound is soluble in water at a concentration of greater than 10 mg/ml. Nanoparticles generated from water soluble compounds are particularly suited for delivery via transmucosal, sublingual, buccal, rectal, vaginal routes, where there is a need for rapid dissolution and absorption, and where there is minimal body fluid available for dissolution.

The phrase "poorly water soluble or substantially water insoluble" for purposes of the present invention means that the compound dissolves in water, particularly at 20° C., at a concentration of 10 mg/ml or less, preferably 5 mg/ml or less, and most preferably less than about 1 mg/ml. When present in the form of large particles, these compounds are typically insufficiently absorbed at the gastrointestinal tract when they are administered in the form of conventional solid formulations.

Drugs that are insoluble or poorly soluble in water can have significant benefits when formulated using particle sizes of 3000 nm or less in diameter. Useful drug classes appropriate for formulation using nanoparticles include proteins, peptides, active agents, analgesics, anti-inflammatory agents, anthelmintics, anti-allergenics, anti-arrhythmic agents, antibiotics, anticoagulants, anticonvulsants/antiepileptics, antidepressants, antidiabetic agents, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, contrast media, corticosteroids, cough suppressants, diagnostic agents, diagnostic imaging agents, diuretics, dopaminergics, haemostatics, immunological agents, lipid regulating agents, muscle relaxants, parasympathomimetic, parathyroid calcitonin, prostaglandins, radio-pharmaceuticals, sex hormones, sleeping aids, stimulants, sympathomimetics, thyroid agents, vasodilators, and xanthines. The treatment of deficiency diseases, alcohol abuse, drug abuse, and many others could be improved with intravenous administration of particulate suspensions of the appropriate drug. Other medical applications for using nanoparticles will be apparent to those skilled in the art.

A preferred class of poorly soluble or practically insoluble drugs are steroids, especially neuroactive steroids such as 3α-hydroxy-3β-methyl-5α-pregnan-20-one (ganaxolone), 3α-hydroxy-3β-trifluoromethyl-19-nor-5β-pregnan-20-one, 2β-ethynyl-3α-hydroxy-5α-pregnan-20-one, and 3α,21-dihydroxy-3β-trifluoromethyl-19-nor-5β-pregnan-20-one.

Specific examples of the slightly water-soluble drugs are coronary vasodilators such as nifedipine, nicardipine, nimodipine, dipyridamole, disopyramide, prenylamine lactate, and efloxate; antihypertensives such as dihydroergotoxine and prazosin; steroidal anti-inflammatory agents such as cortisone, dexamethasone, betamethasone, and fluocinolone acetonide; non-steroidal anti-inflammatory agents such as indomethacin, naproxen, and ketoprofen; psychoneurotic agents such as phenytoin, phenacetamide, ethylphenacetamide, ethotoin, primidone, phensuximide, diazepam, nitrazepam, and clonazepam; cardiac drugs such as digoxin, digitoxin, and ubidecarenon; diuretics such as spironolactone, triamterene, chlorthalidone, polythiazide, and benzthiazide; chemotherapeutics such as griseofulvin, nalidixic acid, and chloramphenicol; skeletal muscle relaxants such as chlorzoxazone, phenprobamate, and carisoprodol; anticonvulsants such as etomidoline; neuroactive steroids and neuroactive semicarbazones as further described herein, antihistaminic agents such as diphenhydramine, promethazine, mequitezine, bisbenthiamine, and clemastine fumarate.

Specific examples of sparingly soluble and soluble drugs are cardiovascular agents such as tamsulosen hydrochloride, lisinopril, enalapril maleate and metroprolol tartrate; central and peripheral nervous system agents such as zolpidem tartrate, fluoxetine hydrochloride, escitalopram oxalate, cyclobenzaprine hydrochloride, queliapine fumarate, elitriptan hydrobromide, and sumatriptan succinate; respiratory agents such as albuterol sulfate; antidiabetic agents such as rosiglitazone maleate and glimepiride; antihistaminic agents such as cetirizide hydrochloride and fexofenadine hydrochloride; and osteoclast mediated bone resorption inhibitors such as alendronate sodium and risedronate sodium.

Other compounds that are suitable for nanosizing include anti-lipidemic drugs, and statins such as atorvastatin calcium, lovastatin, simvastatin, pravastatin sodium, rosuvastatin calcium, and flumastatin sodium, and fenofibrate.

The compounds that are to be processed according to embodiments of the invention can be dissolved either in an aqueous solvent, a non-aqueous solvent or mixed solvents, including mixtures of aqueous solvents, mixtures of non-aqueous solvents, as well as mixtures of non-aqueous and aqueous solvents. Useful non-aqueous solvents include alcohols, halogenated alkanes, dialkylketones and aromatic solvents. Examples of useful non-aqueous solvents include ethanol, preferably 95% ethanol, methanol, isopropyl alcohol, methylene chloride, chloroform, acetone, methylethyl ketone and toluene. An example of a useful aqueous solvent includes water.

Additional solvents that can be used for dissolving compounds include, but are not limited to, acetonitrile, 1-butanol, 2-butanol, chloroform, cyclohexane, 1,2-dichloroethane, dichloromethane, dimethyl sulfoxide, 1,4-dioxane, ethanol, ethyl acetate, hexane, methanol, 2-methoxyethanol, methylbutyl ketone, methylethyl ketone, methylisobutyl ketone, N,N-dimethylacetamide, 1-propanol, 2-propanol, tetrahydrofuran, toluene.

The solution of compound that is to be sprayed may contain other substances that alter the release profile of the compound from the resulting nanometer particle product. These other substances include surface modifiers and surfactants.

A substance that alters the release profile of a compound from a nanoparticle may be used as an additional ingredient to lower the viscosity of the sprayed solution, improve solvent wetting during processing to prevent tile formation of "aggregates," or improve the absorption and uptake by the bodies of animals of poorly soluble active agents. Examples of useful substances that alter the release profile of compounds from nanoparticles include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene caster oil derivatives, polyoxyethylene sorbitan fatty acid esters, polyethylene glycols, polyoxyethylene stearates, colloidol silicon diokide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose, noncrystalline cellulose, magnesium aluminum silicate, triethanolamine, polyvinyl alcohol, and polyvinylpyrrolidone, docusate sodium and sodium lauryl sulfate.

The process of the embodiments of the invention can be practiced with commercially available apparatuses that are equipped with an insert for top spray or bottom spray using a Wurster-type column, or tangential spray using a rotor disk. The design and operation of the sprayer can vary many characteristics of the final product, such as particle size and size distribution, bulk and particle densities, porosity, moisture content, flowability and friability. In the present invention, the design and operation of the sprayer must be such to ensure that the dried particles of compound have an average particle size of less than or equal to 3 microns, preferably less than or equal to 2 microns, more preferably less than or equal to 1 micron. Exemplary conditions are provided for a particular apparatus below. In view of this guidance, one of ordinary skill in the art will be able to adjust apparatus and process parameters to achieve similar results with other sprayers combinations that are available in the art.

Other suitable apparatus will be apparent to those of skill in the art. A suitable apparatus should have multiple functions as described below. Examples include Wurster fluidized bed granulation coaters (such as those produced by Glatt K. K. or Powrex Corporation). This apparatus, which has a cylindrical Wurster column set at the center of a container, is typically employed to fluidize a fine powder or a granulated particle through the column in a single direction by an upward gas stream (jet stream), spray fine droplets of a binder or those of a binder and a surfactant to the subject particle from the jet nozzle at the bottom for coating (bottom spray method), and perform granulation and drying.

In addition to the above-described apparatus, multi-function, combined granulation coaters of the agitating tumbling fluidized bed type (e.g., SPIR-A FLOW granulation coater, produced by Freund Industrial Co., Ltd., and New Marumerizer, produced by Fuji Paudal Co., Ltd.), multi-function combined granulation coaters of the tumbling fluidized bed type (e.g., Multiplex, produced by Powrex Corporation) and other apparatuses can also be used. Spraying methods of these multi-function, combined granulation coaters include the top spraying method, in which droplets are sprayed from the top, the middle spraying (tangential spraying) method, in which droplets are sprayed from a side of the bottom, and the bottom spraying method.

In an embodiment of the present invention, fine droplets of a solution of a compound are sprayed from a jet nozzle into an empty chamber. The gas stream is heated to allow the evaporation of the solvent from the sprayed solution. The use of this apparatus produces a plurality of nanometer sized particles.

A useful bench top system for performing the processes of embodiments of the invention is the FluidAir Model 002. In an embodiment of the invention, the FluidAir Model 002 was used to generate nanoparticles using the following conditions: inlet air temperature of 75-80° C., outlet air temperature of 25-34° C., product temperature of 32-47° C., and a spray rate of 2.2-4.8 g/min.

In a commercial scaled-up process, the following conditions can be used to generate nanoparticles. Useful spray rates are from about 25 to about 50 ml/min, preferably about 30 to about 45 ml/min, and most preferably from about 34 to about 41 ml/min, using one or more spraying nozzles. Static inlet pressure should be controlled to be in the range of about 2 to about 10 bar, preferably about 2.5 to about 8 bar (about 250 to about 800 kPa) affording an air flow of about 20 to about 50 cfm, preferably about 25 to about 45 cfm. Inlet temperature can be about 80° C. to about 100° C., preferably about 85° C. to about 90° C. Product temperature should be about 20° C. to about 60° C., preferably about 25° C. to about 50° C., most preferably about 27° C. to about 48° C.

It is necessary to prevent flocking (aggregation) of the subject compound, and aggregation of the sprayed particles during the process by minimizing the diameter of the droplets of solution of compound that is sprayed. This can be accomplished by using a suitable surfactant in the solution of compound to lower the surface tension and aid in processing.

The concentration/amount of compound, solvent(s), and optional surfactant used for spraying are optionally chosen so that the resulting compound particles have the desired particle size of not more than 3 μm (i.e., 3000 nm), preferably less than or equal to 2 μm (i.e., 2000 nm), and more preferably less than or equal to 1 μm (i.e., 1000 nm).

The particles preferably have a mean diameter of less than 3000 nm, preferably from about 50 nm to about 2000 nm, more preferably about 50 nm to about 1000 nm, even more preferably about 200 nm to about 900 nm, most preferably about 300 nm to about 800 nm.

Particle size in the mixtures can be determined by any number of methods including, a laser diffraction technique using photo correlation spectroscopy (Nicomp C370). The results are typically reported in terms of volume-weighted mean diameter. Volume-weighted mean diameter is defined as follows:

$$(\Sigma nd^4)/(\Sigma nd^3)$$

where n=the number of particles in a size interval characterized by a diameter "d".

The nanosized compound obtained by embodiments of the invention can be formulated in the form of powders, tablets, granules, capsules, aerosols, suspensions, syrups, ointments, suppositories, and the like, with one or more additional pharmaceutically acceptable excipients and/or diluents.

The pharmaceutical compositions obtained using certain embodiments of the invention can be administered to any animal that can experience the beneficial effects of the compounds of the invention. Foremost among such animals are humans, although the invention is not intended to be so limited.

The pharmaceutical compositions obtained using certain embodiments of the invention can be administered by any means that achieve their intended purpose. For example, administration can be by gastrointestinal, nasal, pulmonary, vaginal, rectal, dermal, occular, otic, intramuscular, subcutaneous, and intravenous routes. Alternatively, or concurrently, administration can be by the oral route. The dosage administered will be dependent upon the age, health, and weight of the recipient, kind of concurrent treatment, if any, frequency of treatment, and the nature of the effect desired.

Suitable fillers may be used such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate, croscarmelllose sodium and crospovidone. Auxiliaries are, above all, flow-regulating agents and lubricants, for example, silica, talc, stearic acid or salts thereof, such as, magnesium stearate or calcium stearate, and/or polyethylene glycol. In order to produce coatings resistant to gastric juices, solutions of suitable cellulose preparations, such as, acetylcellulose phthalate or hydroxypropylmethyl cellulose, are used. Dye stuffs or pigments can be added to the tablets, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the nanoparticle active compounds that may be further mixed with fillers such as lactose, binders such as starches, and/or lubricants such as talc or magnesium stearate and, optionally, stabilizers. In soft capsules, the active compounds are preferably suspended in suitable liquids, such as, fatty oils or liquid paraffin. In addition, stabilizers may be added.

The following examples are illustrative, but not limiting, of the method and compositions of the present invention. Other suitable modifications and adaptations of the variety of conditions and parameters normally encountered, and obvious to those skilled in the art are within the spirit and scope of the invention.

Example 1

A water insoluble compound was dissolved in a mixture of methanol/acetone. Three solution concentrations of the compound were made with 3, 5, or 15% w/v of the compound. The solutions were sprayed into a FluidAir laboratory scale fluid bed system, Model 002 equipped with a bottom spray Wurster configuration. The inlet air temperature was maintained from about 66-83° C. The outlet air temperature is monitored and recorded during the process, and ranged from 26-34° C. The spray rate ranged from 2.2-4.8 grams/minute. The air atomization pressure was maintained at 30 psi. The three resultant materials had a mean particle size (mean diameter) of 772, 769, and 777 nanometers for the 3, 5, and 15% w/v solution sprayed respectively.

Example 2

The above compound was dissolved in methanol/acetone as the solvent with added ingredients, sodium lauryl sulfate (7% w/v) and hypromellose (1% w/v) to achieve a 5% w/v solution of the compound. The same process conditions were maintained and the resultant material had a mean particle size of 743 nanometers. The material demonstrated enhanced dispersion and wetting characteristics when exposed to water.

Example 3

Atorvastatin calcium was dissolved in methanol and 0.6% w/v of docusate sodium. The solution was sprayed using essentially the same process conditions as described in Example 1 and 2. The resultant material had a mean particle size of 733 nanometers.

Example 4

The spray-dried compound powder was tested for its bioavailability in dogs, in comparison with a formulation of the same compound formulated by traditional procedures. The bioavailability of the nanosized spray-dried compound, based on the maximum plasma concentration and the plasma area-under-the-curve concentration, was determined to be superior to that of the traditional (micronized) formulation.

Having now described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A process for producing particles wherein the particles are produced by:
   preparing a solution of a pharmaceutical compound in a liquid medium in which the compound is dissolved; and
   spraying the solution of the dissolved compound into an empty heated chamber at a rate of 25 to 50 ml/min, wherein the spraying step produces particles of the compound having a mean diameter of 50 nm to 3000 nm in the heated chamber.

2. The process of claim 1, wherein said particles of said compound have a mean diameter from about 1000 nm to about 2000 nm.

3. The process of claim 1, wherein said particles of said compound have a mean diameter of less than 1000 nm.

4. The process of claim 1, wherein the resulting particles of said compound have a mean diameter of about 50 nm to about 1000 nm.

5. The process of claim 1, wherein the resulting particles of said compound have a mean diameter of about 300 to about 800 nm.

6. The process of claim 1, wherein the compound is substantially water insoluble.

7. The process of claim 6, wherein the liquid medium comprises at least one non-aqueous solvent.

8. The process of claim 1, wherein the liquid medium comprises at least one aqueous solvent.

9. The process of claim 1, wherein the chamber comprises a heated, fluidized bed of carrier particles.

10. The process of claim 1, wherein the compound solution comprises a carrier molecule.

11. The process of claim 1, wherein said compound is selected from proteins, peptides, active agents, analgesics, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, prostaglandins, radio-pharmaceuticals, sex hormones, anti-allergic agents, stimulants, sympathomimetics, thyroid agents, vasodilators and xanthines.

12. The process of claim 10, wherein said carrier molecule is selected from the group consisting of xylitol, mannitol, sorbitol, arabinose, ribose, xylose, glucose, mannose, galactose, sucrose, lactose, sodium lauryl sulfate, docusate sodium and hydroxy propyl methyl cellulose.

13. The process of claim 1, wherein said spraying step occurs from one or more spraying nozzles in an apparatus equipped with an insert for (a) top spray using a Wurster-type column, (b) bottom spray using a Wurster-type column, or (c) tangential spray using a rotor disk.

14. The process of claim 1, wherein said dissolved compound solution further comprises one or more other substances that alter the release profile of the compound from the resulting particles.

15. The process of claim 14, wherein said one or more other substances are surface modifiers or surfactants.

16. The process of claim 14, wherein said one or more other substances are selected from the group consisting of gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene caster oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, and polyvinylpyrrolidone.

17. The process of claim 1, wherein said particles are combined with a pharmaceutically acceptable carrier or diluent to form a pharmaceutical composition.

18. The process of claim 17, wherein said composition is administered to a user.

19. The process of claim 18, wherein said administration occurs via oral gastrointestinal delivery, buccal delivery, sublingual delivery, pulmonary delivery, nasal delivery, vaginal delivery, rectal delivery, ocular delivery, otic delivery, epidermal delivery, dermal delivery or parenteral delivery.

* * * * *